US009681660B2

(12) United States Patent
Murray

(10) Patent No.: US 9,681,660 B2
(45) Date of Patent: Jun. 20, 2017

(54) PENTACHLOROPHENOL/BORATE COMPOSITIONS AND USES THEREOF

(75) Inventor: Gordon Murray, North River (CA)

(73) Assignee: Stella-Jones Inc., Saint-Laurent, Quebec (CA)

( * ) Notice: Subject to any disclaimer, the term of this patent is extended or adjusted under 35 U.S.C. 154(b) by 0 days.

(21) Appl. No.: 14/366,594

(22) PCT Filed: Dec. 30, 2011

(86) PCT No.: PCT/IB2011/003293
§ 371 (c)(1),
(2), (4) Date: Jul. 21, 2014

(87) PCT Pub. No.: WO2013/098579
PCT Pub. Date: Jul. 4, 2013

(65) Prior Publication Data
US 2014/0342172 A1 Nov. 20, 2014

(51) Int. Cl.
| | | |
|---|---|---|
| *A01N 31/10* | (2006.01) | |
| *A01N 55/08* | (2006.01) | |
| *B27K 3/08* | (2006.01) | |
| *B27K 3/16* | (2006.01) | |
| B27K 3/50 | (2006.01) | |
| B27K 3/34 | (2006.01) | |
| B27K 3/40 | (2006.01) | |

(52) U.S. Cl.
CPC ............. *A01N 31/10* (2013.01); *A01N 55/08* (2013.01); *B27K 3/08* (2013.01); *B27K 3/163* (2013.01); *B27K 3/34* (2013.01); *B27K 3/40* (2013.01); *B27K 3/50* (2013.01); *Y10T 428/31989* (2015.04); *Y10T 428/662* (2015.04)

(58) Field of Classification Search
CPC .................................... B27K 3/08; B27K 3/02
See application file for complete search history.

(56) References Cited

U.S. PATENT DOCUMENTS

| | | | | |
|---|---|---|---|---|
| 2,051,486 | A | 10/1934 | Kautter | |
| 2,182,081 | A * | 12/1939 | Hatfield | B27K 3/50 |
| | | | | 106/16 |
| 3,518,348 | A * | 6/1970 | Dulat | A01N 59/14 |
| | | | | 424/660 |
| 3,574,855 | A * | 4/1971 | Brown | A01N 31/10 |
| | | | | 514/347 |
| 3,600,408 | A | 8/1971 | Bursack et al. | |
| 3,956,100 | A | 5/1976 | Todd | |
| 3,960,969 | A | 6/1976 | Greco et al. | |
| 4,051,282 | A * | 9/1977 | Davies | B27K 3/08 |
| | | | | 422/28 |
| 4,076,871 | A * | 2/1978 | Short | B27K 3/0278 |
| | | | | 106/18.12 |
| 4,234,665 | A | 11/1980 | Johnson | |
| 4,461,721 | A * | 7/1984 | Goettsche | A01N 59/14 |
| | | | | 106/18.13 |
| 4,585,795 | A | 4/1986 | Linderborg | |
| 4,929,454 | A | 5/1990 | Findlay | |
| 5,080,935 | A * | 1/1992 | Kelso, Jr. | B27K 1/00 |
| | | | | 34/404 |
| 5,098,472 | A | 3/1992 | Watkins et al. | |
| 5,104,664 | A | 4/1992 | Palmere et al. | |
| 5,246,652 | A * | 9/1993 | Hsu | B27N 9/00 |
| | | | | 252/607 |
| 5,296,240 | A | 3/1994 | Palmere et al. | |
| 5,447,686 | A | 9/1995 | Seidner | |
| 5,460,816 | A | 10/1995 | Palmere et al. | |
| 5,641,726 | A | 6/1997 | Walker | |
| 5,645,828 | A | 7/1997 | Palmere et al. | |
| 5,700,841 | A | 12/1997 | Walker | |
| 5,709,821 | A | 1/1998 | von Bonin et al. | |
| 5,891,921 | A | 4/1999 | Walker | |
| 5,958,463 | A | 9/1999 | Milne et al. | |
| 6,087,303 | A | 7/2000 | Walker | |
| 6,103,387 | A | 8/2000 | Yamamoto et al. | |
| 6,426,095 | B2 | 7/2002 | Palmere et al. | |
| 6,630,174 | B2 | 10/2003 | Palmere et al. | |
| 6,953,501 | B2 | 10/2005 | Kelley et al. | |
| 7,128,778 | B2 | 10/2006 | Thompson | |
| 7,597,902 | B2 | 10/2009 | Lloyd et al. | |
| 8,465,780 | B2 | 6/2013 | Lloyd | |
| 8,709,462 | B2 | 4/2014 | Lloyd et al. | |
| 2003/0199655 | A1 | 10/2003 | Yurugi et al. | |
| 2004/0028934 | A1 | 2/2004 | Preston et al. | |
| 2005/0013939 | A1 * | 1/2005 | Vinden | B27K 3/0214 |
| | | | | 427/325 |
| 2005/0186352 | A1 * | 8/2005 | Hutter | B27K 3/0292 |
| | | | | 427/430.1 |
| 2007/0042161 | A1 | 2/2007 | Gibbs | |
| 2007/0151476 | A1 | 7/2007 | Humar et al. | |
| 2008/0221067 | A1 * | 9/2008 | Hoffman | A01N 43/653 |
| | | | | 514/64 |
| 2009/0069271 | A1 * | 3/2009 | Stanimiroff | B27K 3/36 |
| | | | | 514/64 |
| 2010/0297204 | A1 * | 11/2010 | Uhr et al. | 424/405 |
| 2011/0039031 | A1 * | 2/2011 | Cobham | B27K 3/52 |
| | | | | 427/427.7 |
| 2012/0148859 | A1 | 6/2012 | Cobham | |

FOREIGN PATENT DOCUMENTS

GB          0 249 698          4/1926

OTHER PUBLICATIONS

Landroodi et al. S96: Bioremoval of Pentachlorophenol (PCP) in biodisel versis diesel carriers, SIM Annual Meeting and Exhibition, Jul. 26, 2011.*
Webb et al., 1958 Cooperative Creosote Project-XIV: 35 Years of Field Experience with Posts, AWPA Proceedings, 1995, vol. 91, pp. 120-125.
International Search Report for PCT/IB2011/003293, mail date Aug. 10, 2012, 2 pages.

(Continued)

*Primary Examiner* — David Turocy
(74) *Attorney, Agent, or Firm* — Foley & Lardner LLP

(57) ABSTRACT

Disclosed is a wood preservative composition comprising: an ester of boric acid; pentachlorophenol (PCP); and American Wood Preservative Association's (AWPA) P9 Type A solvent. The composition is useful for reducing insect and microbial decay in wood. Further disclosed are methods of making and using such compositions.

26 Claims, No Drawings

(56) References Cited

OTHER PUBLICATIONS

Langroodi et al., Proceedings of the 107$^{th}$ Annual Meeting of the American Wood Protection Association, May 15-17, 2011 (May 15, 2011), p. 117.
Lebow et al., USDA Forest Service Research Note FPL-RN-0295, 6 pp. (Apr. 2005).
Lesar et al., Performance of Boron-ethanolamine-quaternary Ammonium Based Wood Preservatives Against Leaching, Wood Decay and Blue Stain Fungi, Wood Research, 2008, vol. 53, No. 3, p. 17-26.
Roll, "Wood Preservation Category 4b, Study Guide for Commercial Applicators", Ohio Department of Agriculture—Pesticide Regulation—Certification and Training, Aug. 2003, 3 pps. Access from: <URL: http://pested.osu.edu/documents/CommStudy/4b%20Wood%20Preservation.pdf> p. 28 under E. Pentachlorophenol Solutions.
Roll, D., "Wood Preservation Category 4b, Study Guide for Commercial Applicators," Ohio Department of Agriculture—Pesticide Regulation—Certificate and Training, Aug. 2016, pp. 1-59, XP055074601.

\* cited by examiner

PENTACHLOROPHENOL/BORATE COMPOSITIONS AND USES THEREOF

BACKGROUND OF THE INVENTION

Wood products have been used as utility poles, railway ties, and construction materials in a wide variety of industries. Without proper treatment, wood products deteriorate and are susceptible to weathering, insects (e.g., termites, carpenter ants, and beetles), marine borers (e.g., mollusks and crustaceans), bacteria, and fungi (e.g., stains, white rot, soft rot, and brown rot). Wood treatment is required to prevent these problems.

Borate compounds contain oxoanions of boron in a +3 oxidation state. The simplest borate ion, $BO_3^{3-}$, and its acidic counterpart, boric acid $B(OH)_3$, have trigonal planar structures. Other borates include trigonal $BO_3$ or tetrahedral $BO_4$ structural units, sharing oxygen atoms. A number of polymeric borate ions are known. They may be made by reacting $B(OH)_3$ or $B_2O_3$ with metal oxides. Examples include: diborate $B_2O_5^{4-}$ (e.g., $Mg_2B_2O_5$), triborate $B_3O_7^{5-}$ (e.g., $CaAlB_3O_7$), tetraborate $B_4O_9^{6-}$ (e.g., sodium tetraborate $Na_2B_4O_7 \cdot 10H_2O$), pentaborate $B_5O_6(OH)_4^-$ (e.g., sodium pentaborate $Na[B_5O_6(OH)_4] \cdot 3H_2O$), and octaborate (e.g., disodium octaborate tetrahydrate, Tim-Bor, $Na_2B_8O_{13} \cdot 4H_2O$).

Borates, such as octaborate, are broad spectrum insecticides commonly used in the treatment of wood. They have the advantage of being readily diffusible into the interior of wood and exhibit low mammalian toxicity. Solid rods of boric acid, for example, are driven into the base of previously installed utility poles to prolong the life of the pole. Once inserted, the boric acid diffuses into the interior of the pole to protect the base region of the pole. However, the installation of boric acid rods is costly and labor intensive because trenches must be dug around the poles, the base must be drilled, and the rods inserted. Replacement boric acid rods must then be reinserted numerous times during the lifetime of the pole. Further, borates are susceptible to leaching and may not adequately protect against soft rot fungi.

Pentachlorophenol (PCP) is a broad spectrum biocide (e.g., insecticide, bactericide, and herbicide), used for the surface treatment of wood. PCP is an effective biocide due, in part, to its ability to inhibit oxidative phosphorylation. Solutions of PCP for the surface treatment of wood are commonly formulated in a solvent classified by the American Wood Preservative Association (AWPA) as P9 Type A oil. The AWPA P9 Type A oil comprises a "hydrocarbon solvent" and an "auxiliary solvent" which, in combination, have physical characteristics, as mandated by the AWPA, that are related to viscosity, distillation characteristics, flash point, specific gravity, and the solubility of PCP. However, PCP has the disadvantage that it is not readily diffusible into the interior of wood and may fail to protect the center "heartwood."

As such, a single and stable wood preservative composition is needed that readily diffuses into the interior of wood to protect the heartwood, while also providing adequate treatment at the surface. Methods of applying such wood preservative composition are likewise needed that are less costly and time consuming.

SUMMARY OF THE INVENTION

Disclosed herein is a stable wood-preservative composition comprising borate esters and pentachlorophenol (PCP) in AWPA P9 Type A oil. Also disclosed is a one-step process for treating wood with the disclosed wood-preservative composition.

It was found that some wood preservative compositions comprising borates and PCP in AWPA P9 Type A solvent were difficult to obtain as a homogenous solution, unless excessive and cost-prohibitive quantities of solvent were used to keep the borates and PCP dissolved during storage and transport. In fact, borates proved more difficult to dissolve in a PCP/AWPA P9 Type A solvent system than in other common wood preservative solvents such as creosote. Creosote comprises over 300 different compounds, the majority of which are polycyclic aromatic hydrocarbons, having assorted bond resonance and electron induction properties that help to dissolve borates. Creosote tends to keep solutes dissolved despite disturbances to the solution, such as changes in pressure or temperature. Conversely, the PCP molecule is a much simpler monocyclic ring, and AWPA P9 Type A oil, generally comprising diesel and biodiesel hydrocarbons, has less bond resonance and fewer electron induction properties relative to creosote. Thus, borate solutions of PCP in AWPA P9 Type A oil are more difficult to maintain as a homogenous solution that can withstand significant iceberging of the borates. "Iceberging" is the industry term used to describe borates that precipitate in storage tanks, delivery pipes, and at the joints of pipes.

It was also found that, upon usage, when some preservative solutions of borates in a PCP/AWPA P9 Type A solvent were infused into wood under pressure, the borates tended to react with wood constituents, such as wood sugars, tannins, and acids, and the resulting borate complexes further precipitated.

In response to these problems, wood preservative compositions comprising borate esters in PCP/AWPA P9 Type A solvent were developed as homogenous solutions, that remained so upon storage and handling, and that could be readily infused into wood, such as utility poles, railroad ties, and dimensional timber, without causing the borate esters to precipitate from solution.

In one aspect, a composition is provided which comprises an ester of boric acid; pentachlorophenol (PCP); and American Wood Preservative Association's (AWPA) P9 Type A solvent.

In another aspect, a wood preservative composition is provided consisting essentially of: an ester of boric acid; pentachlorophenol (PCP); and American Wood Preservative Association's (AWPA) P9 Type A solvent.

In another aspect, wood is provided, where the wood is coated with or immersed in a composition of the present technology as described herein.

In another aspect, a method of treating wood is provided that comprises the steps of: immersing the wood in the treatment solution that comprises a composition of the present technology as described herein; and pressure impregnating the immersed wood above 1 atm (101.325 kPa). The method causes the release of boron from the boron ester of boric acid and causes the boron to migrate into the interior of the wood.

In another aspect, wood is provided, where the wood is treated according to the method of the present technology.

DETAILED DESCRIPTION OF THE INVENTION

Borates and PCP are particularly difficult to dissolve in a minimal and economically feasible volume of solvent such as AWPA P9 Type A solvent. Conversely, creosote more readily dissolves borate compounds. Thus, borate ester compositions were developed with improved solubility in PCP/AWPA P9 Type A solvent systems. Further, methods were developed to maintain the solubility of borate esters in PCP/AWPA P9 Type A solvent systems during storage, handling, and while the wood preservative composition is being impregnated into wood.

In one aspect, a composition is provided comprising: an ester of boric acid; pentachlorophenol (PCP); and American Wood Preservative Association's (AWPA) P9 Type A solvent. In certain embodiments, the composition of the above aspect comprises a sufficient volume of another cosolvent or additive to maintain stability (i.e., solubility) of boron-containing ingredients within the composition.

In another aspect, a wood preservative composition is provided consisting essentially of: an ester of boric acid; pentachlorophenol (PCP); and American Wood Preservative Association's (AWPA) P9 Type A solvent. The term "consisting essentially of" is meant to encompass, within the composition of the above aspect, a sufficient volume of another cosolvent or additive to maintain stability (i.e., solubility) of boron-containing ingredients within the composition. Thus, in certain embodiments, the composition of the above aspect includes a sufficient volume of another cosolvent or additive to maintain stability (i.e., solubility) of boron-containing ingredients within the composition.

In certain embodiments, the composition has about 0.01 wt % to about 75 wt % of the ester of boric acid. In certain embodiments, the composition has about 0.01 wt % to about 25 wt % of the ester of boric acid. In certain embodiments, the composition has about 1 wt % to about 15 wt % of the ester of boric acid. In other embodiments, the composition has about 1 wt % to about 5 wt % of the ester of boric acid. In certain embodiments, the composition has about 5 wt % of the ester of boric acid. In other embodiments, the composition has about 4 wt % of the ester of boric acid. In certain embodiments, the composition has about 3 wt % of the ester of boric acid. In other embodiments, the composition has about 2 wt % of the ester of boric acid. In certain embodiments, the composition has about 1 wt % of the ester of boric acid. In certain embodiments, the composition has about 0.01 wt % to about 1 wt % of the ester of boric acid. Unless indicated otherwise, all percentages provided throughout this specification are weight percentages (e.g., wt % or w/w %).

A wide variety of esters of boric acid may be used in the present compositions, including but not limited to alkanol, alkenol, alkanolamine esters and mixtures of any two or more. For example, in some embodiments, the ester of boric acid is a $C_1$-$C_{22}$ alkanol ester of boric acid. In certain embodiments, the ester of boric acid is a $C_1$-$C_{12}$ alkanol ester of boric acid. In certain embodiments, the ester of boric acid is a $C_1$-$C_6$ alkanol ester of boric acid. In certain embodiments, the ester of boric acid is a straight chain $C_1$-$C_{22}$ alkanol ester of boric acid. In certain embodiments, the ester of boric acid is a branched $C_1$-$C_{22}$ alkanol ester of boric acid. In certain embodiments, the ester of boric acid is a $C_2$-$C_{22}$ alkenol ester of boric acid. In certain embodiments, the ester of boric acid is a $C_2$-$C_{12}$ alkenol ester of boric acid. In certain embodiments, the ester of boric acid is a $C_2$-$C_6$ alkenol ester of boric acid. In certain embodiments, the ester of boric acid is a monoalkanolamine ester of boric acid. Such an ester of boric acid may be prepared, e.g, from a reaction mixture of about 40 wt % to about 80 wt % boric acid, $C_1$-$C_6$ monoalkanolamine, and water.

In certain embodiments, the composition comprising an ester of boric acid, pentachlorophenol (PCP), and the AWPA P9 Type A solvent is substantially anhydrous. In certain embodiments, the ester of boric acid is substantially anhydrous. In certain embodiments, substantially anhydrous means less than 5 wt % water. In other embodiments, substantially anhydrous means less than 4 wt % water. In certain embodiments, substantially anhydrous means less than 3 wt % water. In other embodiments, substantially anhydrous means less than 2 wt % water. In certain embodiments, substantially anhydrous means less than 1 wt % water. In other embodiments, substantially anhydrous means less than 0.5 wt % water. In certain embodiments, substantially anhydrous means less than 0.1 wt % water. In other embodiments, substantially anhydrous means less than 0.01 wt % water.

In compositions of the present technology, the ester of boric acid may be a monoester, diester, trimester or a mixture of any two or more thereof. For example, a $C_1$-$C_6$ monoalkanolamine ester of boric acid can be a monoester of boric acid, a diester of boric acid, a triester of boric acid or a mixture of any two or more of the foregoing. In certain embodiments, the $C_1$-$C_6$ monoalkanolamine ester is a monoethanolamine ester of boric acid. A $C_1$-$C_6$ monoalkanolamine ester of boric acid is also referred to herein as a "Borate Ester" and comprises any one of the mono, di or tri esters and/or mixtures thereof. In certain embodiments, the monoethanolamine ester of boric acid is prepared and is referred to herein as the "MBE Ester" or "MBE."

The $C_1$-$C_6$ monoalkanolamine ester (e.g., a monoethanolamine or MBE ester of boric acid) is prepared by mixing $C_1$-$C_6$ monoalkanolamine (e.g., monoethanolamine) in an aqueous solution of boric acid and allowing the $C_1$-$C_6$ monoalkanolamine (e.g., monoethanolamine) to react with the boric acid.

The concentration of $C_1$-$C_6$ monoalkanolamine (e.g., monoethanolamine) in the reaction mixture is about 2 wt % to about 43 wt %; the concentration of water in the reaction mixture is about 2 wt % to about 27 wt %; and the concentration of boric acid in the reaction mixture is about 20 wt % to about 80 wt %. Alternatively, the concentration of $C_1$-$C_6$ monoalkanolamine (e.g., monoethanolamine) in the reaction mixture is about 28 wt % to about 38 wt %; the concentration of water in the reaction mixture is about 12 wt % to about 22 wt %; and the concentration of boric acid in the reaction mixture is about 45 wt % to about 70 wt %. In yet another embodiment, the concentration of boric acid in the reaction mixture is about 48 wt % to about 66 wt % with the remainder of the mixture being $C_1$-$C_6$ monoalkanolamine and water, where the wt % of the $C_1$-$C_6$ monoalkanolamine is approximately twice the wt % of the water. The quantity of $C_1$-$C_6$ monoalkanolamine (e.g., monoethanolamine) in the reaction mixture relative to boric acid can be adjusted upward, resulting in greater amounts of di and triester; or downwards, resulting in lesser amounts of di and triester. Because the reaction is exothermic, in certain embodiments, the esterification reaction of boric acid is carried out with cooling. In some embodiments, water is substantially absent from the treatment solution used in the pressure impregnation step. Thus, in certain embodiments, as much water as possible is evaporated away due to the heat that is generated from the exotherm that occurs during the esterification reaction. In some embodiments, the treatment solution used in the pressure impregnation step has greater than or equal to 5 wt % water. In some embodiments, the treatment solution used in the pressure impregnation step has less than 5 wt % water. In some embodiments, the treatment solution used in the pressure impregnation step has less than 2 wt % water. In some embodiments, the treatment solution used in the pressure impregnation step has less than 1 wt % water.

The Borate Ester solution (i.e., the reaction product of boric acid and the $C_2$-$C_6$ alkanolamine, such as MBE prepared from boric acid and ethanolamine) is then blended with PCP in AWPA P9 Type A solvent to form the treatment solution for the pressure impregnation. In some embodiments the Borate Ester solution has greater than or equal to 5 wt % water. In certain embodiments, the Borate Ester solution is substantially water free. In some embodiments the Borate Ester solution has less than 5 wt % water. In some embodiments the Borate Ester solution has less than 4 wt % water. In some embodiments the Borate Ester solution has less than 3 wt % water. In some embodiments the Borate Ester solution has less than 2 wt % water. In some embodiments the Borate Ester solution has less than 1 wt % water. In some embodiments the Borate Ester solution has less than 0.5 wt % water. In some embodiments the Borate Ester solution has less than 0.1 wt % water. In some embodiments the Borate Ester solution is a MBE solution prepared from boric acid and ethanolamine. The temperature of this blending step is not critical, however, the temperature is typically elevated in order to decrease the viscosity of the treatment solution and thereby facilitate the blending and to remove any remaining water present in the Borate Ester solution. As such, the temperature and period of time during which the elevated temperature is maintained is adjusted so that the blend is homogeneously mixed and substantially all water has been removed through evaporation (e.g., greater 95%, greater than 98%, or greater than 99% w/w free of water). Temperatures of about 120 to about 200° F. are commonly used. The final concentration of Borate Ester in the treatment solution is from about 0.01 wt % to about 12 wt %; the final concentration of PCP in the treatment solution is from about 0.01 wt % to about 12 wt %; and the final concentration of AWPA P9 Type A solvent in the treatment solution from about 76 wt % to about 99 wt %. Alternatively, the final concentration of Borate Ester in the treatment solution is from about 3 wt % to about 5 wt %; the final concentration of PCP in the treatment solution is from about 5 wt % to about 9 wt %; and the final concentration of AWPA P9 Type A solvent in the treatment solution is from about 86 wt % to about 92 wt %.

In other embodiments, the ester of boric acid is prepared from a reaction mixture of about 50 wt % to about 70 wt %; boric acid, $C_1$-$C_6$ monoalkanolamine, and water. In certain embodiments, substantially all of the water is removed from the ester of boric acid before being added to the composition.

In other embodiments, the ester of boric acid is a $C_1$-$C_6$ monoalkanolamine ester of boric acid. In certain embodiments, the $C_1$-$C_6$ monoalkanolamine ester of boric acid is a monoethanolamine ester of boric acid. In other embodiments, the monoethanolamine ester of boric acid is a mixture of the mono, di, and triester of boric acid.

In certain embodiments, the composition has about 1 wt % to about 40 wt %; of the pentachlorophenol (PCP). In certain embodiments, the composition has about 1 wt % to about 20 wt % of the pentachlorophenol (PCP). In other embodiments, the composition has about 3 wt % to about 12 wt % of the pentachlorophenol (PCP). In certain embodiments, the composition has about 4 wt % to about 9 wt % of the pentachlorophenol (PCP). In other embodiments, the composition has about 8 wt % of the pentachlorophenol (PCP).

Pentachlorophenol (PCP) is an aromatic alcohol that has been used as a broad spectrum biocide in many applications. These include uses as an insecticide, bactericide, herbicide, algicide and molluscide. Pentachlorophenol is an effective biocide due, in part, to its ability to inhibit oxidative phosphorylation by making cell membranes more permeable to protons. This results in a change in the cell's electrical potential.

In its raw form, PCP is crystalline and yellow to brown in color. It is generally used industrially as large blocks of approximately 2,000 kg or as bags of small pellets, each about 1 to about 2 g in weight. Industrial grade PCP can be produced, for example, by the chlorination of phenol or by the hydrolysis of hexachlorobenzene. Industrial grade PCP may contain contaminants, such as chlorophenol isomers (e.g., trichlorophenol or tetrachlorophenol), predioxins, isopredioxins, dioxins, and furans. Certain grades of PCP may contain as little as from about 85% to about 95% PCP. In certain embodiments, technical grade PCP is at least 97% pure. (e.g., PCP from Vulcan Chemicals Inc.) In certain embodiments, the PCP is converted to a phenolate salt such as sodium pentachlorophenate (NaPCP).

In certain embodiments, the American Wood Preservative Association's (AWPA) P9 Type A solvent comprises a "hydrocarbon solvent" and an "auxiliary solvent" which, in combination, satisfy the following physical characteristics as shown in Table 1:

TABLE 1

Physical Characteristics of AWPA P9 Type A Solvent

| Physical Characteristic | Requirement for P9 Type A Solvent |
| --- | --- |
| Distillation | at least 50% at 490° F. (254° C.) |
| | at least 90% at 585° F. (307° C.) |
| Viscosity at 100° F. (38° C.) | at least 37.5 Saybolt Universal Seconds (SUS) |
| Flash Point | at least 150° F. (66° C.) |
| PCP solvency | at least 10 grams of PCP dissolve in 90 grams of whole oil |
| | the oil fraction that is un-distilled above 260° C. dissolves at least 6 grams of PCP per 100 mL oil |
| Water and sediment | at or below 5,000 ppm |
| Specific gravity | at least 0.91 |

"Hydrocarbon solvents" are solvent fractions derived from crude petroleum or high temperature coal tar by common refining processes such as distillation separation, extraction, or by catalytic or thermal rearrangement of the carbon-hydrogen structure of the hydrocarbons of such solvent fractions. In certain embodiments, the hydrocarbon solvent comprises diesel.

"Auxiliary solvents" or "co-solvents" include hydrocarbon moieties derived from petroleum products or agricultural sources. The auxiliary solvent is generally blended with the hydrocarbon solvent to improve its physical characteristics, and make those physical characteristics conform to AWPA P9 Type A specifications.

In certain embodiments, the auxiliary solvent is biodiesel. Biodiesel generally comprises hydrocarbon compounds, predominantly a mixture of $C_{10}$-$C_{22}$ hydrocarbons, some with one or more double bonds, and each with a terminal alkyl ester moiety. In certain embodiments, biodiesel comprises biodiesel methyl esters. In certain embodiments, the biodiesel comprises one or more of the following: canola methyl esters (CME), cotton seed methyl esters (CSME), corn methyl esters (COME), used vegetable oil methyl esters (UVO), fatty acid methyl esters (FAME), palm methyl esters (PME), and soy methyl esters (SME). In certain embodiments, the biodiesel comprises soy methyl esters (SME). In certain embodiments, the auxiliary solvent comprises an aromatic solvent. In certain embodiments, the auxiliary solvent comprises naphtha. In certain embodiments, the auxiliary solvent comprises an alcohol. In certain embodiments, the auxiliary solvent comprises an ether.

In certain embodiments, the AWPA P9 Type A solvent comprises a hydrocarbon solvent and an auxiliary solvent, where the hydrocarbon solvent comprises diesel and the auxiliary solvent comprises biodiesel. In certain embodiments, the hydrocarbon solvent comprises diesel and the auxiliary solvent comprises soy methyl esters (SME).

In certain embodiments, the AWPA P9 Type A solvent is about 50 wt % to about 99 wt % diesel and about 1 wt % to about 50 wt % biodiesel. In other embodiments, the AWPA P9 Type A solvent is about 70 wt % to about 80 wt % diesel and about 20 wt % to about 30 wt % biodiesel. In certain embodiments, the AWPA P9 Type A solvent is about 75 wt % diesel and about 25 wt % biodiesel. In certain embodiments, the biodiesel comprises soy methyl esters (SME).

In other embodiments, the composition has an open-cup flashpoint of at least 60° C. In certain embodiments, the composition has an open-cup flashpoint of at least 66° C. In open cup devices for the measurement of flash points, the sample is contained in an open cup which is heated, and at intervals a flame is brought over the surface. The measured flash point will actually vary with the height of the flame above the liquid surface. The best known example is the Cleveland open cup (COC).

Alternatively, the flashpoint of the composition may be measured using closed-type testers. There are two types of closed cup testers: non-equilibrium, such as Pensky-Martens where the vapors above the liquid are not in temperature equilibrium with the liquid, and equilibrium, such as Small Scale (commonly known as Setaflash) where the vapors are deemed to be in temperature equilibrium with the liquid. Both of these types the cups are sealed with a lid through which the ignition source can be introduced. Closed cup testers normally give lower values for the flash point than open cup (typically about 5° C. to about 10° C. lower, or about 9° F. to about 18° F. lower) and are generally regarded as an approximation of the temperature at which the vapor pressure reaches the lower flammable limit.

The flash point is an empirical measurement rather than a fundamental physical parameter. The measured value will vary with equipment and test protocol variations, including temperature ramp rate (in automated testers), time allowed for the sample to equilibrate, sample volume, and whether the sample is stirred.

In other embodiments, the composition is a substantially homogenous solution. In certain embodiments, the composition is a substantially homogenous solution at a temperature of about 15° C. to about 35° C. In certain embodiments, the composition is a substantially homogenous solution at a temperature of about 15° C. to about 35° C. for up to one month. In certain embodiments, the composition is a substantially homogenous solution at a temperature of about 15° C. to about 35° C. for up to one week. In certain embodiments, the composition is a substantially homogenous solution at a temperature of about 25° C. In certain embodiments, a solution is deemed a substantially homogenous solution when suspended solids within the solution are equal to or less than 5 wt %. In certain embodiments, suspended solids within the solution are equal to or less than 4 wt %. In certain embodiments, suspended solids within the solution are equal to or less than 3 wt %. In certain embodiments, suspended solids within the solution are equal to or less than 2 wt %. In certain embodiments, suspended solids within the solution are equal to or less than 1 wt %. In certain embodiments, suspended solids within the solution are equal to or less than 0.5 wt %. In certain embodiments, suspended solids within the solution are equal to or less than 0.25 wt %. In certain embodiments, suspended solids within the solution are equal to or less than 0.1 wt %.

In another aspect, wood is provided, where the wood is coated with or immersed in a composition according to any of the above embodiments. In certain embodiments, the wood is a utility pole. In certain embodiments, the wood is a railroad tie. In certain embodiments, the wood is a dimensional timber.

In another aspect, a method of treating wood is provided comprising the steps of immersing the wood in the treatment solution comprising the composition of any of the above embodiments; and pressure impregnating the immersed wood above 1 atm (101.325 kPa); which cause the release of boron from the $C_1$-$C_6$ monoalkanolamine ester of boric acid and which cause the boron to migrate into the interior of the wood.

In certain embodiments, the method is a one-step process for treating wood to prevent or reduce insect or microbial decay. The wood is coated or immersed in a treatment solution comprising a $C_1$-$C_6$ monoalkanolamine ester of boric acid (e.g., monoethanolamine ester of boric acid), PCP, and AWPA P9 Type A solvent. The coated or immersed wood is then exposed to conditions that are suitable for causing release of boron from the borate ester and which cause the released boron to migrate into the interior of the wood.

The disclosed one-step process is more convenient than the two step "envelope" treatment process that is common in the industry for treating wood with boric acid. In the two step treatment process, the wood is first immersed in a boric acid solution and set aside for about six weeks under cover, thereby allowing the borate to diffuse throughout the wood. This first step is followed by a second step, treatment of the borate-infused wood with, for example, creosote, to form a hydrophobic envelope around the borate-infused wood. This second step, the creosote envelope, prevents leaching of the borate solution from the wood.

However, the two-step envelope treatment suffers from serious drawbacks. First, the first step requires up to six weeks of borate treatment to diffuse into the wood, which is extremely time consuming and inefficient. Up to several additional weeks may be required for the borate-infused wood to dry before the second encapsulation step can be implemented with creosote. Finally, extra handling and equipment are required to carry out the two-step process.

Thus, an improved one-step process was developed. To carry out the disclosed one-step processes, the wood being treated to reduce insect and/or microbial decay is immersed in the treatment solution and subjected to conditions that cause boron to be released from the Borate Ester and to migrate into the interior of the wood. Boron is thus transferred into the wood from the carrier solution comprising PCP and AWPA P9 Type A solvent. The transferred boron reacts quickly to form the boric acid equivalent ($B_2O_3$). This boric acid equivalent is exchanged with oxygen containing ligands, including water, within the wood. The boron moves from the PCP and AWPA P9 Type A solvent in response to the higher moisture content in the core of the wood and the polar environment at the core of the heartwood. The boric acid equivalent migrates primarily as $B_2O_3$ but may also react with the numerous wood sugars, tannins, acids, and natural decay resistant chemicals such as tropolones and stilbenes to form numerous borate complexes.

The disclosed one-step process is more convenient and economical than the conventional two-step process to treat wood. Furthermore, the disclosed one-step process effectively treats wood with borate ester using PCP and AWPA P9 Type A solvent.

For example, pressure impregnation is suitable for use in the disclosed one-step process. Pressure impregnation is merely used in the second step of the prior two-step process, during the application of an envelope coating of preservative to the wood being treated. Alternatively, in the disclosed one-step process, pressure impregnation is used to both (a) apply the envelope coating of Borate Ester in PCP and AWPA P9 Type A solvent, and (b) to cause the Borate Ester to decompose and release boron and to cause the released boron to migrate into the interior of the wood.

Pressure impregnation refers to subjecting wood that is immersed in the treatment solution of Borate Ester, PCP, and AWPA P9 Type A solvent, to elevated temperature and pressure for a period of time sufficient to achieve release of boron and migration of the released boron throughout the interior of the wood. The disclosed methods thereby achieve a sufficient concentration of boron within the wood to reduce insect and microbial degradation. Suitable concentrations of boron in the interior of the wood are at least 0.05 pounds per cubic foot (pcf) of Boric Acid Equivalent (BAE) of $B_2O_3$. In certain embodiments, suitable concentrations of boron in the interior of the wood are at least 0.11 pcf of BAE of $B_2O_3$. The precise temperature and pressure can vary according to the thickness and type of wood and length of the treatment time. The person of ordinary skill will be able to determine suitable parameters to achieve a suitable concentration and distribution of boron by monitoring the migration of the boron throughout the interior of the wood by, for example, atomic absorption. Alternatively, argon plasma screening with AWPA boron stain, can be used to confirm presence or absence of boron in the wood (AWPA A3-08-17, 2010). Treatment parameters can then be adjusted accordingly. Commonly used conditions for the pressure impregnation of borate ester and PCP, using AWPA P9 Type A solvent, include a pressure of about 100 psi to about 160 psi and a temperature of about 120° F. to about 170° F. (49° C. to about 77° C.). Alternative conditions include a pressure of about 130 psi to about 160 psi and a temperature of about 120° F. to about 150° F. (49° C. to about 66° C.). In certain embodiments, the treatment time is at least 10 minutes. In certain embodiments, the treatment time is about 10 minutes to about 10 hours. In certain embodiments, the treatment time is about 20 minutes to about five hours.

The pressure impregnation is carried out in a pressure vessel. Exemplary pressure vessels include cylindrical retorts that are 5 feet to 8 feet in diameter, with lengths up to 200 feet, which allow for the uniform application of temperature, air, fluid pressure, and vacuum. The wood may be placed into the retort on a small railcar or tram. A working solution tank is used to fill the cylinder with the wood present under various pressure and temperature conditions. The retort holds the wood immersed in the chosen treating solution and allows for control of pressure through fluid pumps and air compressors, temperature with heat exchange coils, and vacuum with liquid ring pumps. These systems are designed to give uniform conditions throughout the volume of the retort so that all areas of the wood are subjected to equal temperature and pressure conditions. Pressure vessels are commercially available from any large steel fabrication facility. Regulations for their design vary from state to state and country to country.

For example, the wood may be treated by loading it into a pressure cylinder, where it is given initial air pressure (e.g., about 138 kPa to about 500 kPa) to fill the wood cells with air. The cylinder is then filled with preservative, which has optionally been preheated (e.g., approximately 90° C.), while using a controlled venting procedure to maintain the pressure in the wood cells. A desired fluid pressure of the preservative is reached (e.g., approximately 1000 kPa) and maintained for several hours depending on the wood species. A "pumping out" of the pressure cylinder then occurs and the "gross retention" of preservative within the wood is determined. If this gross retention is found to be within an acceptable range, a vacuum is applied in order to remove any additional free preservative product. At the end of this process there is a "net retention" of preservative. A final steaming can optionally be performed to clean the wood with a short terminal vacuum. The wood can then be bored as per Canadian Standards Association (CSA) specifications and a pass or fail designation is determined based on penetration and retention of preservative within a specified zone of the wood.

Methods of treating wood as described herein may include any equipment which is commonly available to the skilled artisan: a pressure cylinder, heating source, working tank, storage tank, and a mix tank. This equipment may be automated. The "pressure cylinder" is a long cylindrical tube which contains the wood and preservative mixture and is designed to handle pressures of up to 2500 kPa. A "heat source" allows for maintenance of elevated temperatures within the pressure cylinder and any of the tanks, provides heat for post pressure steaming, and/or to "dry" the wood by boiling it in preservative solution. A "working tank" generally maintains 7-9% PCP in P9 solvent. This tank is generally used to empty and fill the pressure cylinder. A "storage tank" generally stores the P9 solvent and feeds this P9 solvent into the "mix tank" where it is combined with PCP. A "mix tank" is where the PCP is dissolved in the P9 solvent.

Following pressure impregnation, the wood is separated from the treatment solution. When the process is carried out in a pressure vessel, this is typically accomplished by releasing the pressure and pumping the treatment solution out of the pressure vessel. However, any other suitable means of separating a solid from a liquid can be used, including filtration or centrifugation.

In one embodiment, the cylinder is pressurized with air before it is filled with the treatment solution. This step is referred to herein as "Pretreatment Pressurization." Suitable pressures range from atmospheric pressure to 75 psi. Alternatively, the pressure ranges from 0-25 psi. The Pretreatment Pressurization typically lasts from about 10 minutes to about 10 hours. Alternatively, the Pretreatment Pressurization lasts from about 10 minutes to about 3 hours. In another embodiment, the Pretreatment Pressurization lasts from about 20 minutes to about one hour. Following Pretreatment Pressurization, the pressure is maintained while the wood is immersed in the treatment solution for pressure impregnation.

Following the pressure impregnation and separation of the wood from the treatment solution, the wood can be subjected to an expansion bath. An expansion bath is used to minimize leaching and bleeding after treatment and to remove excess preservative from the surface of the wood. Bleeding refers to the flow of preservative solution from the interior of the wood to the surface of the wood. Leaching, which comprises bleeding, refers to the runoff of excess preservative solution from the surface of the wood to the surrounding environment.

Subjecting the wood to an expansion bath refers to immersing the wood in a higher temperature oil and subjecting the oil and immersed wood to elevated temperatures, typically a temperature higher than what was used for the pressure impregnation, typically from about 10° F. to about 40° F. higher; alternatively from about 10° F. to about 20° F. higher. Temperatures of about 140° F. to about 180° F. (about 60° C. to about 82° C.) are commonly used, alternatively from about 130° F. to about 160° F. (about 54° C. to about 71° C.). The duration of exposure of the expansion bath is at least 30 minutes, alternatively from about 0.5 hours to about five hours. In another embodiment, the duration of the expansion bath is from about one to two hours. Examples of suitable high temperature oils include the oils used in the pressure impregnation (e.g., AWPA P9 Type A solvent with or without PCP). For example, the oil mixture used for the pressure impregnation can be conveniently used for the expansion by adjusting the temperature upwards. When the expansion bath treatment is completed, the oil is separated from the wood. When the process is carried out in a pressure cylinder, the oil is typically pumped out of the apparatus. Other suitable separation methods can also be used, e.g., filtration. The separation of the oil from the wood is considered herein to be part of the expansion bath.

The expansion bath treatment and separation of the oil (e.g., AWPA P9 Type A solvent with or without PCP) from the treated wood is typically followed by vacuum treatment to remove residual liquid. The final vacuum is carried out at pressures of least 10 inches of mercury and typically about 15 to about 40 inches, more commonly about 20 to about 28 inches of mercury. The duration of the vacuum treatment is for at least 15 minutes, alternatively from about 0.5 to about ten hours, and in another embodiment from about 0.5 to about five hours, and in another embodiment from about 0.5 to about two hours.

The Lowry Process and Ruepig Process are well known in the art for applying an envelope coating of PCP and AWPA P9 Type A solvent to wood. Both of the processes are suitable for the disclosed one-step wood treatment process for impregnating wood with boron and envelope coating the wood with compositions comprising a boron ester, PCP, and AWPA P9 Type A solvent. The Lowry Process and Ruepig Process are described more fully in the AWPA (AWPA T1-10, 2010).

The prior two-step process often requires the use of wood that is dry, i.e., has a moisture content of about 20 wt % to about 40 wt %. Because the moisture content of most wood is greater than about 20 wt % to about 40 wt %, a drying step is often necessary before the prior two-step process can be employed. Moisture can be removed from wood by, for example, immersing the wood in oil at elevated temperature under vacuum, e.g., at around 180° F. at 24 inches Hg. While the disclosed process can readily treat "dry" wood, one advantage of the disclosed one-step process compared with the prior two-step process is that wood does not need to be rigorously dried in order to be treated by the disclosed one-step process. Specifically, the disclosed one-step process can also be used to treat wood that is "semi dry" (i.e., a moisture content of about 40 wt % to about 70 wt %) and "wet" (i.e., a moisture content above 70% wt %). Moreover, the disclosed process is not limited to any particular type of wood. Examples of wood that can be used in the disclosed process include, but are not limited to, Pine (e.g., Red Pine, Jack Pine, Southern Yellow Pine, Lodgepole Pine), Fir (e.g., Douglas Fir), Western Red Cedar, Spruce, Eastern and Western Hemlock, and hardwoods (e.g., Oak). Wood is commonly in the form of a cant when treated according to the disclosed process. A cant is the square section of timber that follows the removal of the outer bark. In certain embodiments of the method, the treatment reduces insect and/or microbial decay in the wood.

In other embodiments of the method, the pressure impregnation is carried out at a pressure of about 100 psi to about 160 psi (689 kPa to about 1,103 kPa) and a temperature of about 120° F. to about 170° F. (about 49° C. to about 77° C.). In certain embodiments of the method, the pressure is applied gradually at a rate of about 1 psi/min to about 20 psi/min (about 7 kPa/min to about 138 kPa/min). In certain embodiments of the method, the pressure is applied gradually at a rate of about 1 psi/min to about 5 psi/min (about 7 kPa/min to about 34 kPa/min).

In other embodiments, the method further comprises separating the wood from the treatment solution after the pressure impregnation. In certain embodiments, the method further comprises separating the wood from the treatment solution after the pressure impregnation; and exposing the wood to an expansion bath. In other embodiments, the method further comprises exposing the wood to a vacuum below 1 atm (101.325 kPa) after completion of the expansion bath. In certain embodiments of the method, the vacuum is applied gradually at a rate of about 1 psi/min to about 5 psi/min (about 7 kPa/min to about 34 kPa/min).

In certain embodiments of the method, the wood is a mixed softwood cant. In other embodiments of the method, the wood is a mixed hardwood cant. In other embodiments of the method, the wood is a round utility pole with the outer bark removed. In other embodiments of the method, the wood is a vascular cambium. In certain embodiments of the method, the moisture content of the wood is greater than 40 wt %. In other embodiments of the method, the pressure impregnation is carried out according to the Lowry or Rueping process.

In another aspect, wood is provided, where the wood is treated according to any of the above embodiments of the method. In certain embodiments, the wood is a utility pole. In certain embodiments, the wood is a railroad tie. In certain embodiments, the wood is a dimensional timber.

The invention is illustrated by the following examples which are not intended to be limiting in any way.

EXAMPLES

Example 1

The Preparation of 50 MBE

50 Monoethanolamine Borate Ester (50 MBE) was prepared from approximately 50 wt % boric acid, approximately 33 wt % monoethanolamine and approximately 17 wt % water. To a clean dry kettle was added monoethanolamine (5,750 pounds, 2,608 kg, 33 wt %). Water (3,010 pounds, 1,365 kg, 17 wt %) was then added. Boric acid (8,450 pounds, 3,833 kg, 50 wt %) was added, 8-10 bags at a time, with agitation and cooling. The boric acid was allowed to mix for 10 minutes before additional boric acid was added in 8-10 bag quantities. The reaction was exothermic and the temperature was maintained at about 140° F. to about 150° F. (about 60° C. to about 66° C.). After the addition of boric acid was complete, the reaction mixture was maintained with heating at about 140° F. to about 150° F. (about 60° C. to about 66° C.). Once the boric acid had dissolved completely, the base number was tested. Once the base number was about 8 to about 20, the reaction was filtered through 1 micron pores into T60 drums.

Example 2

Tim-Bor Solubility Tests

All boron sources used were AWPA 2010 compatible and expressed as a Boric Acid Equivalent (BAE) of $B_2O_3$. 52 Monoethanolamine Borate Ester (52 MBE) was prepared analogously to Example 1 from approximately 52 wt % boric acid, approximately 24 wt % monoethanolamine, and approximately 24 wt % water. PCP/P9 contained 8 wt % PCP and 92 wt % P9.
  Treatments: 52 MBE
  Monoethanolamine
  Biodiesel
  10 wt % of 52 MBE and 90 wt % PCP/P9
  Control: Water
  Replications: Each treatment was replicated three times.
  Method: 40 g, 50 g, 60 g, 70 g, and 80 g of Tim-Bor (disodium octaborate tetrahydrate or D.O.T.) were added to round bottomed flasks containing 100 mL of each Treatment solution. The flasks were then attached to a rotary evaporator (Büchi R-124) for 1 hour at 60 rpm and a temperature of 80° C.
  Qualitative determinations were made of whether the boron source dissolved in each Treatment solution, based on the presence or absence of clumps or clouds of boron. The flasks were then capped and allowed to cool for 24 hours at which time the Treatment solutions were re-inspected to determine whether the boron source remained dissolved.
  Results: The 52 MBE Treatments, with and without PCP/P9, were the only ones to dissolve all quantities of Tim-Bor up to 80 grams.

Example 3

Solubility of Boric Acid and MBE in a PCP/P9 Solvent System

Boric acid and/or 52 MBE were added to PCP/P9 solvent (having 8 wt % PCP and 92 wt % P9). The resulting Treatments were used to treat wooden stakes. The diffusion of borate into the treated wooden stakes was observed.
  Treatments: 10 wt % Boric Acid and 90 wt % PCP/P9
  10 wt % Boric Acid, 10 wt 52 MBE, and 80 wt % PCP/P9
  10 wt 52 MBE and 90 wt % PCP/P9
  5 wt % Boric Acid and 95 wt % PCP/P9
  5 wt % Boric Acid, 5 wt % 52 MBE, and 90 wt % PCP/P9
  5 wt % 52 MBE and 95 wt % PCP/P9
  Control: 100 wt % PCP/P9
  Replications: each Treatment was applied to four stakes.
  Method: Twenty-eight Red Pine stakes were cut measuring 2 in×2 in×12 in each. Each preservative Treatment (2 L) was used to charge a mini-pilot wood treating plant (Canadian Erectors Manufacturing Ltd.) The wood stakes were treated using the Lowry process with a steam coil heater operating at 180° F. during the initial bath and pressure cycle. Each charge took approximately 6 hours. Following each charge, two of the four stakes were wrapped in plastic wrap, and two stakes were left unwrapped. All stakes were stored in a covered bin in an unheated building. The stakes were tested for borate diffusion at three and six weeks using AWPA method A3-08 (Method for determining penetration of boron-containing preservatives and fire retardants). At the end of each sampling period, a wrapped and unwrapped stake from each treatment was cut in half and the cut edge was sprayed with an indicator solution to determine the extent of borate diffusion into the wood.
  Results: After three weeks of storage the stakes were tested for boron diffusion. Following an application of the indicator solutions (AWPA method A3-08), it was observed that each sample, except the control sample, turned an orange/red color, which indicated that boron had diffused through the wood. The stakes were tested again at six weeks with the same diffusion results.
  The indicator solution tests showed that the color intensity and depth of boron diffusion was much higher for treatments with 52 MBE. There was a large increase in boron concentration in the wood treated with 5 wt % Boric Acid and 5 wt % 52 MBE, and 10 wt % Boric Acid and 10 wt 52 MBE.

Example 4

The Solubility of MBE in a PCP/P9 Solvent System

The objective was to determine the maximum amount of boron that could be incorporated into an MBE product solution. Varying percentages boric acid, monoethanolamine, and water were reacted to give various MBE Treatment formulations.
  Treatments: 52 MBE (52 wt % boric acid, 24 wt % monoethanolamine and 24 wt % water)
  55 MBE (55 wt % boric acid, 22 wt % monoethanolamine and 23 wt % water)
  60 MBE (60 wt % boric acid, 20 wt % monoethanolamine and 20 wt % water)
  70 MBE (70 wt % boric acid, 15 wt % monoethanolamine and 15 wt % water)
  Control: 40 MBE (40 wt % boric acid, 30 wt % monoethanolamine and 30% water)
  Replications: Three replications were run per treatment
  Method: Esterification reactions were undertaken to prepare 40 MBE to 70 MBE formulations (i.e., Treatments) from ethanolamine and increasing amounts of boric acid. Then, fifteen 4 L metal containers were each half-filled with the appropriate 40, 52, 55, 60, or 70 MBE Treatment. The contents were agitated by stirring and the solutions were allowed to coat the sides of the containers. This sequence was used to mimic the commercial handling and storage of preservative solutions. The containers were then allowed to sit undisturbed for one week. The container contents were checked daily for boron precipitants or deposits.
  After one month, some containers containing MBE solutions showed degrees of precipitation proportional to their initial boric acid concentrations. The solutions were analyzed on a scanning electron microscope (SEM) to determine the extent of precipitation. Consequently, a pressurized filtration system was used (from the Pall Corporation, Port Washington, N.Y). The filtration step reduced, and in some cases eliminated, the incidence precipitation and yielded stable boric acid solutions of up to 66 MBE in PCP/P9. Filtered solutions having up to 60 MBE in PCP/P9 were obtained in large volumes.
  Some of these solutions of MBE in PCP/P9 were diluted with about 1 wt % to about 25 wt % biodiesel. For example, the 60 MBE in PCP/P9 was diluted with 5 wt % biodiesel without the substantial formation of precipitants. 60 MBE in PCP/P9 was used in the remaining experiments.

Example 5

Efficacy Testing of Wood Treated by the Disclosed Compositions

ASTM test fungi in Petri dishes were subjected to 60 MBE Treatment solutions with and without PCP/P9. The agar plate test method allowed for rapid determinations of antifungal efficacy against wood-degrading strains of concern. The certified cultures were obtained from the American Type Culture Collection (ATCC) and propagated as per the product information sheets:

*Irpex lacteus*: ATCC number 11245, yeast medium Difco 0712 (ATCC medium no. 200)

*Neolentius lepideus*: ATCC number 12653, YM agar Difco 0712 (ATCC medium no. 200)

*Postia poria*: ATCC number 11538, YM agar Difco 0712 (ATCC medium no. 200)

*Pleurotus ostreatus*: ATCC number 32237, YM agar Difco 0712 (ATCC medium no. 200)

*Trametes versicolor*: ATCC number 42462, Hagem's-Modess medium (ATCC medium no. 479)

*Gleoephyllum trabeum*: ATCC number 11539, Potato Dextrose Agar with 0.5% yeast extract (ATCC medium no. 337)

Each plate was inoculated in a flame induced sterile environment with a 5 mm diameter agar plug. Plates subsequently received surface application of 0.5 mL and 1.0 mL of the Treatment solutions. The plates were incubated for 14 days at 30° C. and the presence or absence of fungal growth was noted and measured.

Results are shown in Tables 2 and 3. PCP/P9 includes 8 wt % PCP and 92 wt % P9. "3% 60 MBE/P9" includes 3 wt % of 60 MBE and 97 wt % of P9. "6% 60 MBE/P9" includes 6 wt % of 60 MBE and 94 wt % of P9. "3% 60 MBE/PCP/P9" includes 3 wt % of 60 MBE and 97 wt % of PCP/P9. "6% 60 MBE/PCP/P9" includes 6 wt % of 60 MBE and 94 wt % of PCP/P9. PCP/P9 includes 8 wt % PCP and 92 wt % P9. The growth of fungi was inhibited at all concentrations and additions of the proposed boron esters, with and without PCP and P9 solvent. Some plates showed minor cross contamination of bacterial colonies at all additions. Bacterial contamination appeared randomly, over the surface of the plates, at both strengths of boron esters. Photos of representative plates can be found in FIG. 1. The results indicate that the boron alone was sufficient to inhibit the fungal growth without PCP. This is key to the stand alone nature of the boron antifungal activity in the heartwood.

TABLE 2

Agar Plate Testing with 1 mL MBE solutions and MBE/PCP blends (as 3% and 6% solutions).

| | | | 60 MBE/P9 Blends | | 60 MBE/PCP/P9 blends | |
|---|---|---|---|---|---|---|
| Fungi | Replications | Control | 3% 60 MBE | 6% 60 MBE | 3% 60 MBE | 6% 60 MBE |
| 11245 | 7 | FPG | NG | NG | NG | NG |
| 12653 | 7 | FPG | NG | NG | NG | NG |
| 11538 | 7 | FPG | NG | NG | NG | NG |
| 32237 | 7 | FPG | NG | NG | NG | NG |
| 42462 | 7 | FPG | NG | NG | NG | NG |
| 11539 | 7 | FPG | NG | NG | NG | NG |

*FPG—Full growth of Fungi on Plate Agar
**NG—No Growth of Fungi on Plate Agar

TABLE 3

Agar Plate Testing with 0.5 mL MBE solutions and MBE/PCP blends (as 3% and 6% solutions).

| | | | 60 MBE/P9 Blends | | 60 MBE/PCP/P9 blends | |
|---|---|---|---|---|---|---|
| Fungi | Replications | Control | 3% 60 MBE | 6% 60 MBE | 3% 60 MBE | 6% 60 MBE |
| 11245 | 7 | FPG | NG | NG | NG | NG |
| 12653 | 7 | FPG | NG | NG | NG | NG |
| 11538 | 7 | FPG | NG | NG | NG | NG |
| 32237 | 7 | 95% | NG | NG | NG | NG |
| 42462 | 7 | FPG | NG | NG | NG | NG |
| 11539 | 7 | FPG | NG | NG | NG | NG |

*FPG—Full growth of Fungi on Plate Agar
**NG—No Growth of Fungi on Plate Agar

Example 6

Soil Block Efficacy Testing

Testing with Soil-Block Cultures:

Standard soil block efficacy testing experiments and soil bed testing experiments can be conducted according to the AWPA guidelines.

For example, mixed hardwood blocks (from about 14 mm to about 19 mm) were tested at various weight percentages of MBE in a PCP/P9 solvent system, in a five step retention series. Treated blocks were exposed to the destructive species of fungi outlined above for periods of up to 16 weeks at about 25° C. to about 27° C. and about 65% to about 75% relative humidity. Efficacy was evaluated as mass loss on each block, according to method E10-09 in the AWPA 2011 standards.

Results showed very small mass loss with 1 wt % to 8 wt % MBE in PCP and P9. The blocks retained the majority of their pre-exposure weights as shown in Table 4. PCP/P9 includes 8 wt % PCP and 92 wt % P9. Some mass losses were expected from the volatization of the PCP and P9 oil. Mass loss was lower than mass loss from creosote-boron treated blocks. Table 5 shows no differences in mass loss between PCP/P9 alone and PCP/P9 and boron. Again, PCP/P9 includes 8 wt % PCP and 92 wt % P9.

TABLE 4

Mass loss (%) of soil blocks when subjected to conditions outlines in AWPA E10-09.

| | | | 60 MBE/PCP/P9 blends (mass loss %) | | | | |
|---|---|---|---|---|---|---|---|
| Fungi | Replications | Control % mass loss | 1% 60 MBE | 2% 60 MBE | 3% 60 MBE | 5% 60 MBE | 8% 60 MBE |
| 11245 | 7 | 70 | 2 | 1 | 1 | 0 | 1 |
| 12653 | 7 | 40 | 1 | 2 | 3 | 1 | 1 |
| 11538 | 7 | 48 | 2 | 0 | 1 | 1 | 2 |
| 32237 | 7 | 60 | 2 | 0 | 1 | 3 | 2 |
| 42462 | 7 | 60 | 1 | 1 | 0 | 2 | 1 |
| 11539 | 7 | 54 | 1 | 0 | 0 | 3 | 1 |

TABLE 5

Mass loss (%) of soil blocks when subjected
to conditions outlines in AWPA E10-09.

| Fungi | Repli-cations | Control % mass loss | PCP/P9 | 3% 60 MBE in PCP/P9 | 4% 60 MBE in PCP/P9 |
|---|---|---|---|---|---|
| 11245 | 7 | 62 | 3 | 1 | 0 |
| 12653 | 7 | 40 | 1 | 1 | 2 |
| 11538 | 7 | 47 | 0 | 2 | 1 |
| 32237 | 7 | 50 | 1 | 2 | 2 |
| 42462 | 7 | 70 | 1 | 0 | 1 |
| 11539 | 7 | 50 | 0 | 0 | 2 |

** No significant differences with respect to type of treatment.

Example 7

MBE Additions do not Materially Affect the Properties of PCP/P9 Solvent

Experiments were undertaken to determine whether the MBE additions materially affect the properties of the PCP/P9 solvent system (per the AWPA 2010 specification P1-P13-09 and P2-09). Table 6 shows the comparison of a 10 wt % 60 MBE in 90 wt % PCP/P9 solvent, as compared with the PCP/P9 solvent alone.

The AWPA P9 Type A oil was prepared from a blend of diesel and biodiesel to meet the following AWPA requirements, as shown in Table 6. Again, PCP/P9 includes 8 wt % PCP and 92 wt % P9.

TABLE 6

Distillations were conducted according to methods ASTM D-86 or D-1160;
viscosity testing was conducted according to methods ASTM D-445 or
D-88; and flashpoints were conducted according to method ASTM D-93.

| | | Formulation | | |
|---|---|---|---|---|
| Physical Characteristic | Requirement for P9 Type A Solvent | PCP/P9 | 10% 60 MBE in 90% PCP/P9 | P9 (100%) |
| Distillation | at least 50% at 490° F. (254° C.) | pass | pass | pass |
| | at least 90% at 585° F. (307° C.) | pass | pass | pass |
| Viscosity at 100° F. (38° C.) | at least 37.5 Saybolt Universal Seconds (SUS) | pass | pass | pass |
| Flash Point | at least 150° F. (66° C.) | pass | pass | pass |
| PCP solvency | at least 10 grams of PCP must dissolve in 90 grams of whole oil | pass | pass | pass |
| | 100 mL oil of the oil fraction that is un-distilled above 260° C. must dissolve at least 6 grams of PCP | pass | pass | pass |
| Water and sediment | at or below 5,000 ppm | pass | pass | pass |
| Specific gravity | at least 0.91 | pass | pass | pass |
| Maximum dioxin/furan concentration | no 2, 3, 7, 8 dioxins | pass | pass | pass |

Example 8

Stability of MBE in a PCP/P9 Solvent System

In some instances, maintaining the solubility of MBE in a PCP/P9 solvent system was dependent upon the effect of vacuum levels and the rapidity with which vacuum levels were increased and decreased during the impregnation of the wood. During the impregnation process, treatment under pressure can cause the wood chemicals from the sapwood and heartwood to dissolve into the P9 solvent, sometimes causing the MBE to precipitate from solution. Such precipitation during the impregnation process was not encountered, for example, when MBE was impregnated using a creosote solvent. Maintaining the solubility of MBE and PCP (and any wood chemicals) in P9 solvent thus required gradual changes in temperature and/or pressure to prevent borate crystallization and a thickening and/or darkening of the P9 solvent.

Pilot plant quantities (e.g., 300 gallons) of 60 MBE in PCP/P9 were taken through various cycles of temperature, pressure, and vacuum to determine the optimum conditions that prevent precipitation. Typical cycles included pressures of about 100 psi to about 160 psi (689 kPa to about 1,103 kPa), temperatures of about 100° F. to about 170° F. (about 38° C. to about 77° C.), and vacuums of about 20 inches Hg to about 27 inches Hg.

The same cycles of temperature, pressure, and vacuum were used to treat Red Pine, Southern Yellow Pine, and Douglas Fir wood samples, with the sapwood and heartwood exposed, with 60 MBE in PCP/P9. Borates were prevented from precipitating from solution when the vacuum was regulated with respect to the volume of air being removed. Relief valves and/or a frequency drives were installed on vacuum pumps to control the volume of air being extracted per second.

Example 9

Improvement of Operational Parameters

In order to optimize the boron penetration and retention during the one-step boron-PCP/P9 treatment process, operational parameters, such as temperature, time, and the length of the pressure cycle were varied to determine how to retain the solubility of MBE and/or the PCP/P9 solvent system. The PCP/P9 solvent system was subjected to lower temperatures relative to creosote-based solvents. For example, the PCP/P9 solvent system was typically subjected to temperatures of about 120° F. to about 170° F. (about 49° C. to about 77° C.). The effect of variable preheating times had little to no effect on the BAE retentions within the wood, suggesting that a minimal preheat time of 1 hour was sufficient for borate retention.

During impregnation of the wood with preservative, the effect of pressure times, which were varied from about 20 minutes to 240 minutes, had little to no effect on the BAE retentions within the wood. This indicated that borate diffusion occurred rapidly within the early stages of the treating cycle. However, increased temperatures during the impregnation step increased borate diffusion. Increasing moisture content of the wood improved the rate of diffusion and allowed wood with high moisture content (e.g., above 40%) to be readily treated by the disclosed one-step method.

Increased percentages of boron within the MBE of the treating solution appears to improve borate retention, in a linear manner, within Red Pine, Southern Yellow Pine, and Douglas Fir. In fact, the more refractory the species of wood, the quickly the boron diffused throughout the wood. All species of wood were easily penetrated with the boron, according to the disclosed single-step method in the PCP/P9 solvent system, and retentions of 2 pounds per cubic foot (pcf) were obtained, which exceeded target retentions of 0.09 pcf $B_2O_3$ or BAE.

Example 10

Treating Cycles for Infusing 60 MBE in PCP/P9 Wood Preservative into Softwood Utility Poles Red Pine Dry: Relatively dry Red Pine utility poles were loaded onto trams and placed into the treatment cylinder. The air pressure was kept at atmospheric pressure or increased to approximately 40 psi (276 kPa), with controlled venting, while filling the cylinder with preservative solution. The temperature was increased to 150° F. (66° C.). The pressure was then gradually increased to approximately 150 psi (1,034 kPa) over 30 min. The pressure was then gradually released over the next 30 minutes and the preservative was pumped from the treatment cylinder. After the preservative was pumped from the treatment cylinder, a vacuum was gradually applied over 20 minutes, reaching the 27 inches of Hg level at the end of the 20 minute period. The vacuum was then released and live steam was injected, to reduce the oil viscosity, for 1 hour at 160° F. (71° C.), followed by a final vacuum for over 30 minutes.

Wet: Moist or wet Red Pine utility poles were placed into the treatment cylinder and only ¾ of the preservative solution was used during the filling step to create an air space. As the oil was heated and a vacuum was applied, moisture from the wet pole was drawn off the top of the cylinder. Heat and vacuum were maintained until the rate of accumulation of water in the steam capture tank is less than 50 gallons per hour. Otherwise, the remaining treatment steps were the same as for dry poles.

Douglas Fir

Dry: Relatively dry Douglas Fir utility poles were loaded onto trams and placed into the treatment cylinder. The air pressure was kept at atmospheric pressure or increased to approximately 60 psi (414 kPa), with controlled venting, while filling the cylinder with preservative solution. The temperature was increased to 160° F. (71° C.). The pressure was then gradually increased to approximately 160 psi (1,103 kPa) over 30 min. Pressure was maintained several hours until gross retention of the preservative solution was achieved. The pressure was then gradually released over the next 30 minutes and the preservative was pumped from the treatment cylinder. After the preservative was pumped from the treatment cylinder, a vacuum was gradually applied over 60 minutes, reaching 27 inches of Hg at the end of the 60 minute period. The vacuum was then released and live steam was injected, to reduce the oil viscosity, for 1 hour at 160° F. (71° C.), followed by a final vacuum for over 60 minutes.

Wet: Moist or wet Douglas Fir utility poles were placed into the treatment cylinder and only ¾ of the preservative solution was used during the filling step to create an air space. As the oil was heated and a vacuum was applied, moisture from the wet pole was drawn off the top of the cylinder. Heat and vacuum were maintained until the rate of accumulation of water in the steam capture tank is less than 50 gallons per hour. Otherwise, the remaining treatment steps were the same as for dry poles.

Southern Yellow Pine

Dry: Relatively dry Southern Yellow Pine utility poles were loaded onto trams and placed into the treatment cylinder. The air pressure was kept at atmospheric pressure or increased to approximately 30 psi (207 kPa), with controlled venting, while filling the cylinder with preservative solution. The temperature was increased to 150° F. (66° C.). The pressure was then gradually increased to approximately 150 psi (1,034 kPa), over 20 min. The pressure was then gradually released over the next 20 minutes and the preservative was pumped from the treatment cylinder. After the preservative was pumped from the treatment cylinder, a vacuum was gradually applied over 20 minutes, reaching 27 inches of Hg at the end of the 20 minute period. The vacuum was then released and live steam was injected, to reduce the oil viscosity, for 1 hour at 160° F. (71° C.), followed by a final vacuum for over 30 minutes.

Wet: Moist or wet Southern Yellow Pine utility poles were placed into the treatment cylinder and steamed while pulling a vacuum to remove moisture. Otherwise, the remaining treatment steps were the same as for dry poles.

Example 11

Treating Cycles for Infusing 60 MBE in PCP/P9 Wood Preservative into Hardwood Utility Poles Hardwood utility poles were subjected to similar Treatment Cycles as those used for Red Pine utility poles. However, an expansion bath was used for one hour at a 10° F. higher temperature, followed by live steaming.

Example 12

Burn Testing

Burn testing is conducted, for example, at the Institute for Combustion Science and Environmental Technology's (IC-SET) gas emissions laboratory in Bowling Green Ky., to confirm that the dioxin and furan levels do not increase upon combustion. Fire retardant properties, which are generally proportional to concentration of boron in the formulation, are also evaluated according to the AWPA specifications.

Example 13

Leaching

The leaching of the poles was tested according to a modified E11-06 AWPA method. Replicates of 8 foot pole sections were leached for a two week periods. Poles treated with a PCP/P9 solvent system alone, and poles treated with MBE in a PCP/P9 solvent system (having a retention of 0.4 pcf BAE), were evaluated. There was no significance difference between the leaching characteristics of these poles.

Example 14

Mechanical Properties

Mechanical properties of the wood were tested in conjunction with Nova Scotia Power's (NSP) Engineering and Operational Groups. Surface hardness, ease of drilling, gaff penetration for climbing the poles, strength, modulus of elasticity (MOE), and modulus of rupture (MOR) were tested as per the ASTM D1036 standard. The gaff penetration and drilling tests were performed by actual linemen, on installed poles treated with the BAE additive, and no issues were noted. Static bending according the ASTM D1036 testing method was performed in the presence of three Engineers from NSP, and all poles passed with excellent deflection upon load indicating higher than acceptable modulus of elasticity and modulus of rupture. For example, a Douglas Fir pole (that is required to take 3700 pounds of force) took over 6000 pounds of force and deflected 12 feet. This result was well above the required average, and indicated that poles treated according to the disclosed one-step procedure with MBE in a PCP/P9 solvent system can withstand an extreme ultimate horizontal breaking force, for example, in the event that an electric line is knocked over.

Example 15

Corrosion Testing

Poles treated according to the disclosed one-step procedure with MBE in a PCP/P9 solvent system undergo minimal corrosion, according to results obtained from ASTM designated tests. Immersion corrosion testing (AWPA standard E-12-94) was conducted to determine the susceptibility of galvanized metal hardware in contact with treated wood to corrosion once installed into utility poles that were:
a) untreated;
b) treated with PCP/P9; or
c) treated with 60 MBE in PCP/P9

This method compared the initial mass of the hardware to that obtained after environmentally accelerated contact with the treated material for a specified period of time. The mass loss was then translated into a projected/anticipated rate of corrosion for that particular metal while in contact with that particular treated product. These tests showed no significant corrosion on galvanized hardware.

Each corrosion simulation was replicated 4 times with 4 bolt clusters for each treatment a), b), and c). Specified AWPA environmental parameters (49±1° C. and 90±1% relative humidity) were applied in accelerate growth chambers for a periods of 240 hours and 480 hours, during which no significant corrosion was noted in any treatments a), b), and c).

Data was statistically analyzed using MINITAB 12 with a Tukey's means comparison test. The statistical output is shown in Table 7. Treatments were not found to be statistically different. For reference, corrosive treating chemicals like Ammonical Copper Zinc Arsenate (ACZA) show 36 mils/year corrosion with galvanized cross arm bolts.

The weight loss of a substrate, after exposure to a corrosive environment, is expressed as mils (thousandths of an inch) per year penetration. Corrosion rate is calculated assuming uniform corrosion over the entire surface of the substrate.

$mpy=(\text{weight loss in grams})*(22,300)/(Adt)$
$mpy=\text{corrosion rate(mils per year penetration)}$ A=area of coupon (square inches)
d=metal density of coupon (g/cm$^3$)
t=time of exposure in corrosive environment (days).

TABLE 7

| Corrosion Rates | |
|---|---|
| Treatment | Corrosion Rate (mpy) |
| untreated | 0.1 |
| treated with PCP/P9 | 0.1 |
| treated with 60 MBE in PCP/P9 | 0.1 |

What is claimed is:
1. A method of treating wood, comprising the steps of:
   a) immersing the wood in a wood treatment composition; and
   b) pressure impregnating the immersed wood at a pressure of about 100 to 170 psi and a temperature of about 100 to 170° F.;
   wherein the wood treatment composition comprises (i) about 3 to 12 wt. % pentachlorophenol (PCP); (ii) at least about 3 wt. % of a borate ester, which comprises a monoalkanolamine borate ester; and (iii) at least about 76 wt. % of an AWPA P9 Type A solvent, which comprises diesel and biodiesel; and
   the wood treatment composition is greater than 98% w/w free of water and is a substantially homogenous solution after storage at a temperature of 15 to 35° C. for one month.
2. The method of claim 1, wherein the borate ester comprises a monoalkanolamine monoethanolamine ester of boric acid.
3. The method of claim 1, wherein the AWPA P9 Type A solvent comprises at least about 50 wt % of the diesel, and about 1 to 50 wt. % of the biodiesel.
4. The method of claim 1, wherein the biodiesel comprises canola methyl esters, cotton seed methyl esters, corn oil methyl esters, palm oil methyl esters, and/or soy oil methyl esters.
5. The method of claim 1, wherein the AWPA P9 Type A solvent has an open-cup flashpoint of at least 66° C., a viscosity of at least about 37.5 Saybolt Universal Seconds at 100° F., and a specific gravity of at least about 0.91.
6. A method of treating wood, comprising the steps of:
   a) immersing the wood in a wood treatment composition; and
   b) exposing the immersed wood from step (a) to conditions which cause boron to migrate into the interior of the wood; wherein the wood treatment composition comprises
   i) pentachlorophenol (PCP);
   ii) borate ester; and
   iii) American Wood Preservative Association's (AWPA) P9 Type A solvent;

and the wood treatment composition is greater than 98% w/w free of water and is a substantially homogenous solution after storage at a temperature of 15° C. to 35° C. for one month; wherein the borate ester comprises a monoalkanolamine borate ester.

7. The method of claim 6, wherein the wood treatment composition comprises a reaction product of a mixture comprising $C_2$-$C_6$ monoalkanolamine and boric acid.

8. The method of claim 6, wherein the borate ester comprises an alkanol, alkenol, and/or alkanolamine ester of boric acid.

9. The method of claim 6, wherein the borate ester comprises a monoethanolamine ester of boric acid.

10. The method of claim 9, wherein the monoethanolamine ester of boric acid is a monoester, diester and/or triester of boric acid.

11. The method of claim 6, wherein the wood treatment composition includes about 3 to 12 wt. % of the pentachlorophenol; and at least about 1 wt. % of an ester of boric acid.

12. The method of claim 6, wherein the AWPA P9 Type A solvent has an open-cup flashpoint of at least 66° C., a viscosity of at least about 37.5 Saybolt Universal Seconds at 100° F., and a specific gravity of at least about 0.91.

13. The method of claim 6, wherein the wood treatment composition further comprises boric acid.

14. The method of claim 6, wherein the wood treatment composition further comprises disodium octaborate tetrahydrate.

15. The method of claim 6, wherein the wood treatment composition comprises (i) about 3 to 12 wt. % of the pentachlorophenol; (ii) at least about 76 wt. % of the AWPA P9 Type A solvent; and (iii) a reaction product of a mixture comprising $C_2$-$C_6$ monoalkanolamine and boric acid, wherein the reaction product includes a $C_2$-$C_6$ monoalkanolamine ester of boric acid.

16. The method of claim 6, wherein the wood treatment composition comprises about 3 to 12 wt. % of the pentachlorophenol; and at least about 76 wt. % of the AWPA P9 Type A solvent.

17. The method of claim 6, wherein the borate ester comprises a monoethanolamine ester of boric acid.

18. The method of claim 6, wherein the wood treatment composition includes at least about 3 wt. % of the borate ester; at least about 76 wt. % of the AWPA P9 Type A solvent; and about 1 to 20 wt. % pentachlorophenol.

19. The method of claim 6, wherein the conditions which cause boron to migrate into the interior of the wood comprise pressure impregnation of the immersed wood.

20. The method of claim 19, wherein the immersed wood is pressure impregnated at a pressure of about 100 psi to about 170 psi and a temperature of about 100° F. to about 170° F.

21. The method of claim 19, wherein the pressure impregnation results in the wood having of boron content of at least about 0.11 pounds per cubic foot (pcf) Boric Acid Equivalent (BAE) of $B_2O_3$.

22. The method of claim 19, further comprising c) separating the treated wood from the treatment solution after the pressure impregnation; d) exposing the treated wood to an expansion bath; e) exposing the treated wood to a vacuum treatment after completion of the expansion bath.

23. The method of claim 22, wherein the AWPA P9 Type A solvent comprises diesel and biodiesel.

24. The method of claim 6, wherein the composition includes at least about 1 wt. % of an ester of boric acid; and about 1 to 20 wt. % pentachlorophenol.

25. The method of claim 6, wherein the conditions which cause boron to migrate into the interior of the wood result in the wood having of boron content of at least about 0.05 pcf BAE of $B_2O_3$.

26. The method of claim 6, wherein the conditions which cause boron to migrate into the interior of the wood comprise pressure impregnation of the immersed wood at a pressure of about 100 psi to about 170 psi and a temperature of about 100° F. to about 170° F.; and the wood treatment composition includes at least about 3 wt. % of the borate ester; at least about 76 wt. % of the AWPA P9 Type A solvent; and about 3 to 12 wt. % pentachlorophenol.

* * * * *

UNITED STATES PATENT AND TRADEMARK OFFICE
CERTIFICATE OF CORRECTION

PATENT NO. : 9,681,660 B2  
APPLICATION NO. : 14/366594  
DATED : June 20, 2017  
INVENTOR(S) : Gordon Murray Page 1 of 1

It is certified that error appears in the above-identified patent and that said Letters Patent is hereby corrected as shown below:

In Column 22, Line 44, Claim 2, please delete "monoalkanolamine".

Signed and Sealed this
Twenty-ninth Day of August, 2017

Joseph Matal
*Performing the Functions and Duties of the*
*Under Secretary of Commerce for Intellectual Property and*
*Director of the United States Patent and Trademark Office*